US010987481B2

(12) United States Patent
Wood

(10) Patent No.: US 10,987,481 B2
(45) Date of Patent: Apr. 27, 2021

(54) SLEEP APNEA NASAL PILLOWS DEVICE

(71) Applicant: REMSleep Holdings Inc, Tampa, FL (US)

(72) Inventor: Thomas Jackson Wood, Waycross, GA (US)

(73) Assignee: REMSleep Holdings Inc., Tampa, FL (US)

(*) Notice: Subject to any disclaimer, the term of this patent is extended or adjusted under 35 U.S.C. 154(b) by 825 days.

(21) Appl. No.: 15/595,990

(22) Filed: May 16, 2017

(65) Prior Publication Data
US 2017/0368285 A1 Dec. 28, 2017

Related U.S. Application Data

(60) Provisional application No. 62/355,493, filed on Jun. 28, 2016.

(51) Int. Cl.
*A61M 16/06* (2006.01)
*A61M 16/20* (2006.01)

(52) U.S. Cl.
CPC .... *A61M 16/0683* (2013.01); *A61M 16/0666* (2013.01); *A61M 16/0611* (2014.02); *A61M 16/208* (2013.01); *A61M 2205/42* (2013.01)

(58) Field of Classification Search
CPC ............ A61M 16/683; A61M 16/0666; A61M 16/0611
See application file for complete search history.

(56) References Cited

U.S. PATENT DOCUMENTS

| 3,145,711 | A | * | 8/1964 | Beber | A62B 23/06 128/204.12 |
|---|---|---|---|---|---|
| 5,533,506 | A | | 7/1996 | Wood | |
| 6,478,026 | B1 | | 11/2002 | Wood | |
| 6,595,215 | B2 | | 7/2003 | Wood | |
| 6,776,162 | B2 | | 8/2004 | Wood | |
| 6,807,967 | B2 | | 10/2004 | Wood | |
| 6,863,069 | B2 | | 3/2005 | Wood | |
| 6,997,177 | B2 | | 2/2006 | Wood | |
| 6,997,187 | B2 | | 2/2006 | Wood et al. | |
| 7,000,613 | B2 | | 2/2006 | Wood et al. | |
| 7,059,328 | B2 | | 6/2006 | Wood | |
| 6,994,089 | B2 | | 7/2006 | Wood | |
| 7,188,624 | B2 | | 3/2007 | Wood | |
| 7,191,781 | B2 | | 3/2007 | Wood | |
| D551,340 | S | | 9/2007 | Wood et al. | |

(Continued)

Primary Examiner — Margaret M Luarca
(74) Attorney, Agent, or Firm — Larson & Larson, P.A.; Frank Liebenow; Justin P. Miller

(57) ABSTRACT

An interface pillow for insertion into a nostril of a user for delivering positive air pressure (e.g. during sleep) has a pliable member having a body. The body has an insertion end and a distal sealing end that includes a seal for interfacing with a cannula. An insertion bulge extends from the body limiting an insertion distance into the user's nostrils. An insertion area of the body extends between the insertion end and the insertion bulge, the sides of which angle inwardly towards the insertion end at an angle. The outer shape of the insertion area is flattened on one side for interfacing with a septum of a nose, and an upper interface area of the outer shape of the insertion area is narrower than a lower interface area of the outer shape of the insertion area to conform to a shape of a nostril of the nose.

11 Claims, 6 Drawing Sheets

(56) References Cited

U.S. PATENT DOCUMENTS

| | | | |
|---|---|---|---|
| 7,472,707 B2 | 1/2009 | Wood et al. | |
| D618,336 S | 6/2010 | Wood | |
| D627,059 S | 11/2010 | Wood et al. | |
| RE42,843 E | 10/2011 | Srickland et al. | |
| 9,138,553 B2 | 9/2015 | Wood | |
| 9,919,121 B2 | 3/2018 | Wood | |
| 2004/0226566 A1* | 11/2004 | Gunaratnam | A61M 16/0666 128/207.18 |
| 2006/0283461 A1* | 12/2006 | Lubke | A61M 16/0666 128/207.11 |
| 2016/0015921 A1* | 1/2016 | Harrison | A61M 16/0683 128/205.25 |
| 2018/0078725 A1* | 3/2018 | Richardson | A61M 16/0666 |

* cited by examiner

SLEEP APNEA NASAL PILLOWS DEVICE

CROSS-REFERENCE TO RELATED APPLICATION

This application claims the benefit of U.S. provisional application No. 62/355,493 filed on Jun. 28, 2016, the disclosure of which is incorporated by reference.

FIELD

This invention relates to the field of medicine and more particularly to a nasal interface for the delivery of gases in the treatment of sleep apnea and other respiratory problems.

BACKGROUND

Ventilation is commonly used in the treatment of respiratory conditions such as sleep apnea. On such form of ventilation is a continuous positive air pressure system often referred to as a CPAP system. Continuous positive air pressure systems typically include a mask that interfaces to a user's mouth or nasal passages, supplying air pressure from an air flow generator that is typically located in the proximity of the user. The mask directs the flow of air into the breathing passage of the user while allowing the user to exhale.

For the treatment of sleep apnea, the continuous positive air pressure system is worn while the user sleeps. In continuous positive air pressure system in which the mask interfaces with the user's nostrils, the nostril interface need be held in place and maintain a seal so that, as the user moves during sleep, the mask/nostril interface remains intact and sealed to provide positive airway pressure.

The mask/nostril interface is often referred to as pillow interfaces that are inserted partially into each nostril, maintaining an air-tight seal. As the pillow interfaces are worn while the user sleeps, it is important that the pillow interfaces be as comfortable as possible. If the seal is not air-tight, less positive airway pressure is delivered and, the break in the seal will often create noise that may impact the user's sleep.

Another issue with continuous positive air pressure system is the flow velocity of the positive airway pressure. In providing an adequate volume of air for each breath the patient takes (inhalation), the continuous positive air pressure system must provide a minimum volume per time period. Tradeoffs are made between providing greater volumes by using larger orifices or by using smaller orifices and increasing the velocity of the provided air. Unfortunately, when the velocity of the provided air is increased, several user issues occur including burning sensations in the user's sinuses, drying of the user's sinuses, a compromised therapeutic index, and increased noise that is undesirable when the user is trying to sleep.

Existing continuous positive air pressure system is that current pillow interfaces are typically round in cross-sectional area. These pillow interfaces cause discomfort when worn as the nasal septum is typically more sensitive to pressure and is typically relatively flat in areas of the nasal openings. Round cross-sectional shapes do not interface well with flat walls and, as an accommodation, prior pillow interfaces are typically made of a soft material that flattens when inserted. This flattening reduces the cross-sectional area of these prior nasal pillows, resulting in an acceleration of the air velocity, and therefore, the issues cited above.

The interface pillows of prior continuous positive air pressure systems have numerous issues, some of which are:

a. Pressure drop within the closed system/cannula.

b. Lack of ability to deliver an adequate volume of inspired air to the patient.

c. Air velocity delivered through these pillow interfaces is often high, leading to burning sensations, drying of sinuses, etc.

d. Such pillows leak if required to deliver more than 10 centimeters of water pressure. Such leaks cause noise disturbances.

e. Such pillow interfaces lead to discomfort at the bottom of the nostrils.

f. Head gear often needs to be adjusted too tight for patient comfort.

g. Air leaks often occur from slight movement of the head.

h. Lower levels of air deliver often lead to a decrease in blood oxygen saturation during sleep.

i. These interfaces pillows fit within the nostrils in a way that leads to a disproportionate amount of pressure being applied against the septum (center cartilage) of the nostrils, causing discomfort. The septum is the most sensitive area of the nostrils.

Many of the above issues relate to the shape of the prior-art interface pillows and the material of which they are made. As the shape of the prior-art interface pillows is not optimal for sealing within the nostrils of a user, to compensate for such, the prior-art interface pillows are made of very soft material that is easily deformed under pressure. The prior-art interface pillows, after insertion, deform to seal within the nostrils of the user. This deformation provides pressure on the sensitive septum of the user's nose, causing discomfort. This deformation also reduces the cross-sectional area of the air passage of each prior-art interface pillow, causing an increase in air flow velocity and noise. The increase in air flow velocity leads to dryness, a sudden burning sensation in the nostrils, and stuffiness in the sinuses. Higher air flow velocity and lower volume of incoming air is less efficient at correcting apnea and often interrupts normal breathing patterns.

Further, most prior interface pillow designs included turning points for the incoming air, some as much as 90 degrees, resulting in turbulence, pressure drop, and a decrease in the therapeutic index of the treatment. As a result of this, more pressure is typically required to deliver the required increased flow rate which partially compensates for inadequate air volume needed for treatment. This increase in air velocity increases unwanted side effects. An increase in air flow velocity is not preferred over supplying adequate air volume.

It should also be noted that with each incremental increase in driving pressure beyond 7 centimeters of water pressure, there is less and less proportionate therapeutic effect. Increases in driving pressure beyond 9 to 10 centimeters of water has little, if any, therapeutic effect using a prior-art interface pillows, and likely only exacerbate the negative effects. Most prior interface pillows will not hold pressures of more than 9 to 10 centimeters of water pressure. This has been one of the significant limitations of such pillow interfaces and only patients with mild obstructive sleep apnea typically have success with the prior interface pillows due to this limitation.

The prior interface pillows create a seal by applying pressure to the bottom of the nose. The seal is tenuous. Head movement often causes a significant and annoying air leak, usually at the outside of the nostrils, unless the head gear is noticeably too tight. The apex of the prior interface pillows (where the air flow passes into the nostrils) is very non-structural and the inner diameter of the prior interface pillows is easily be compromised when pressed against the bottom of the nostrils. This often decreases the cross-sectional flow space and air volume delivered, which in turn, further increases the velocity and/or pressure drop of the air flow entering into the nostrils. The area directly beneath the prior interface pillows where they fit against the nostrils becomes narrowed or compromised when encountering pressure against the bottom of the nose created by the head gear. This creates another source of restriction to air flow resulting in a decrease in delivered air volume, pressure drops, an increase of incoming air velocity, and a reduced positive effect.

Based on typical adult inspiratory demand; a patient's respiratory rate, in many cases, may decrease using the prior interface pillows because less air volume is available, which will take longer to complete the inspiratory cycle. The respiratory rate has been seen to decrease from a normal 12 to 14 breaths per minute down to 9 breaths per minute. This interruption of normal respiratory rate often creates a feeling of suffocation and reduced compliance (usage) of the system.

If the inspiratory cycle is prolonged, the expiratory cycle is also prolonged and the lungs may not empty completely before the inspiratory cycle is initiated. An increase in driving pressure will likely be required, but the increase in driving pressure only partially compensates for the inadequate volume of air that must be delivered to maintain an adequate tidal volume and minute ventilation that feels normal to the user. The result is the user's normal breathing patterns are disrupted, the user feels insecure, a feeling of suffocation and impending doom for some, and less likely to achieve restful sleep. The inadequate lower inspired air volume also creates the need to provide a lower cross-sectional flow space for expired air. The prior interface pillows style interface does not let the patient feel as if their expiratory cycle is normal. This is perceived as an increase in work of breathing. Adequate cross-sectional flow space for exhaled air can only be provided if there is an adequate volume of air supplied to the inspiratory cycle with very little or no resistance accompanied with a low air velocity which simulates normal inspiratory/expiratory flow rate.

The expiratory cycle is normally completed during deep sleep and is achieved only by the elasticity of the patient's lung. Accessory muscles are not active during restful sleep. If inspired air is not normally exhaled the patient will not feel secure and deep sleep will not come easy. The inspired air is not being normally exhaled if the patient's respiratory rate has been disrupted.

Further, bleed ports in prior systems direct exhaled air flow onto the patient's arms/hands. Some bleed ports are embodied into a swivel adaptor that can unintentionally misdirect exhale air flow in an unwanted direction. Constant adjustment is often needed. The patient's breathing mechanics must function as if they are not using CPAP therapy, and the CPAP therapy must correct apneic events to promote a sound, prolonged sleep, and consistent compliance to treatment. For the vast majority of patients using prior interface pillows, this requires a high volume of air delivery; significantly lower air velocity; and using significantly less pressure.

It is desired that the patient experiences no change in noise of air flow throughout the inspiratory/expiratory cycle. Any change in air flow noise during any part of the ventilation cycle indicates the patient's normal breathing is being interrupted. This is typically caused by an inadequate volume of inspired air and inadequate flow space for exhaled air. When a high volume of air is provided then a low level of pressure is required to correct apneic events for the vast majority of patients. Apneic events are not sudden; they build. If an ample/adequate volume of inspired air is supplied with a lower pressure, apneic events are prevented. If adequate inspired air volume is not available, then apneic events eventually occur during sleep and pressure will need to be increased to compensate for inadequate volume. To this end, sleep technicians often increase driving pressures as the sleep cycles progress. The increase in driving pressure is not preferred over adequate volume, often only partially compensates for an air volume deficiency, and typically increases unwanted effects.

Another issue with existing continuous positive air pressure systems is disposal of extra pressure, either from the air flow generator or from the user's exhalation. Many existing continuous positive air pressure systems have inadequate exit venting or exit venting that is directed toward the user's body, creating discomfort as the user exhales.

What is needed is a continuous positive air pressure system that provides interface pillows that seal within nostrils while retaining comfort and proper air flow.

SUMMARY

In one embodiment, an interface pillow for insertion into a nostril of a user is disclosed. The interface pillow has a pliable member having a body. The body has an insertion end and a distal sealing end that includes a seal for interfacing with a cannula. An insertion bulge extends from the body limiting an insertion distance into the user's nostrils. An insertion area of the body extends between the insertion end and the insertion bulge. The insertion area has sides that angle inwardly towards the insertion end at an angle, thereby a cross-sectional area of the insertion end being smaller than a second cross-sectional area at a point where the insertion area interfaces to the insertion bulge. The outer shape of the insertion area is flattened on one side for interfacing with a septum of a nose, and an upper interface area of the outer shape of the insertion area is narrower than a lower interface area of the outer shape of the insertion area to conform to a shape of a nostril of the nose.

In another embodiment, an interface pillow for insertion into a nostril of a user is disclosed. The interface pillow has a pliable member having a body. The body has an insertion end and a distal sealing end that has a seal for interfacing with a cannula. An insertion bulge extends from the body limiting an insertion distance to approximately 0.25 inches. An insertion area of the body extends between the insertion end and the insertion bulge. The insertion area has sides of approximately 0.25 inches in length that taper inwardly towards the insertion end at an angle, thereby a cross-sectional area of the insertion end being smaller than a second cross-sectional area at a point where the insertion area interfaces to the insertion bulge. The outer shape of the insertion area is flattened on one side for interfacing with a septum of a nose. An upper area of the outer shape of the insertion area is narrower than a lower area of the outer shape of the insertion area to conform to a shape of a nostril of the nose.

In another embodiment, a method of delivering positive airway pressure to a user is disclosed including connecting a cannula to a source of air flow. Interface pillows that are sealed to the cannula are inserted into respective nostrils of the user. Each of the interface pillows has an insertion end entering the respective nostril and sealing there within by way of an insertion depth, a taper defined by gradually increasing cross-sectional area of the interface pillow away from the insertion end, and an outer shape at the insertion end. The outer shape at the insertion end is flattened in an area that interfaces with a septum of each respective nostril and is larger at a bottom interface area of the nostril than at a top interface area of the nostril. This provides a positive flow of air from the interface pillows into the user's nostrils.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
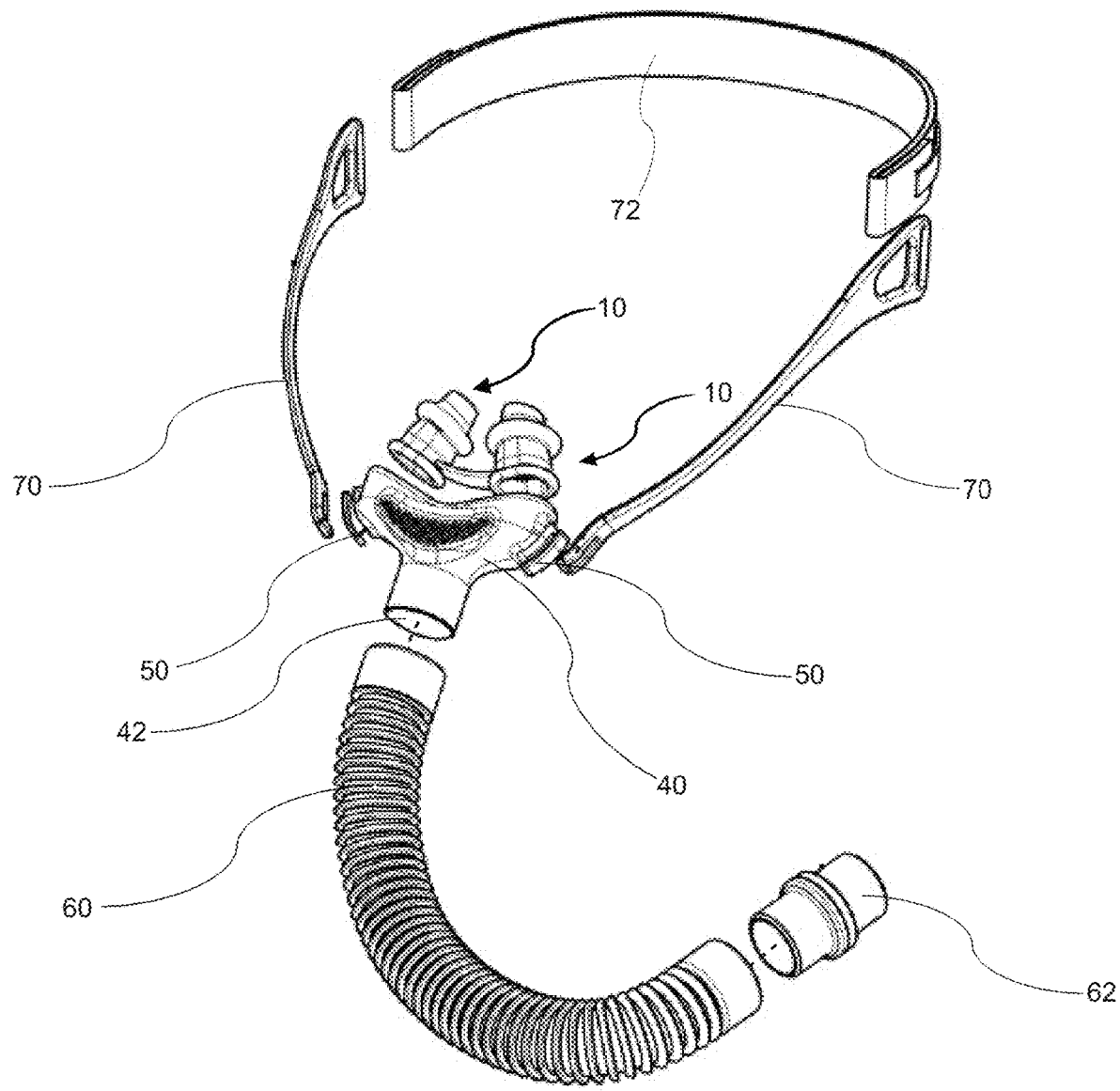
FIG. 1 illustrates a perspective view of a system of the present invention.

Reference will now be made in detail to the presently preferred embodiments of the invention, examples of which are illustrated in the accompanying drawings. Throughout the following detailed description, the same reference numerals refer to the same elements in all figures.

The present invention provides an adequate air volume, allowing for a normal inspiratory cycle and allowing normal adequate exhalation while treating, for example, sleep apneas. The high volume delivery is provided at decreases air flow velocity, increasing lateral pressure, decreasing of the venturi effect, and increasing the effectiveness of treatment. The present invention is designed so as to not interrupt a patient's normal breathing mechanics; therefore, not interrupting a patient's normal respiratory rate and not interrupting a patient's normal inspiratory/expiratory ratio.

Work of breathing greatly diminished. There is reduced turbulence or restriction during the inspiratory cycle with little or no noticeable change in noise throughout the inspiratory/expiratory cycle. The patient is able to exhale completely via the patient's elasticity of the lungs and without the use of any accessory muscles. Respiratory rate typically remains normal at 12 to 14 breaths per minute. The patient maintains normal minute ventilation throughout the night. Heart rate and oxygen saturation remain optimal throughout the night. The patient experiences normal breathing without apneic events. Once initial pressures are set during polysomnography, there is no need for increasing pressures at any time throughout the sleep cycle. These benefits result into a significant increase in compliance to the treatment (e.g., the patient continues to use the system).

Throughout this description, the continuous positive air pressure system is described in relationship to being used by a user, wearer, patient, etc., interchangeably. There is no limitation as to who will used the continuous positive air pressure system described here within.

Referring to FIG. 1, a perspective view of a system of the present invention is shown. The system shown in FIG. 1 is a continuous positive air pressure system that receives air flow from a source (not shown), connected to flexible tube 60 at one end by a swivel adapter 62. Current systems typically provide air flow to the flexible tube 60, which is often a 22 millimeter flexible tube 60. The present application requires a source of air flow, but is in no way limited to any particular source of a gas (e.g. air, concentrated air, oxygen, etc.) and is not limited in any way to specific plumbing for delivery of such air flow.

A distal end of the flexible tube 60 connects to an air supply port 42 of the cannula 40. In general, the cannula is substantially hollow. As the continuous positive air pressure system is typically worn while sleeping, the continuous positive air pressure system need be retained to the person using the continuous positive air pressure system.

Although there is no limitation as to how the continuous positive air pressure system is held to the user, in the embodiment shown, the cannula 40 includes tabs 50 for attaching a retainer 70/72. In some embodiments, the retainer 70/72 includes an adjustable portion 72 for conforming to a head size of a wearer (e.g. having hook/loop material adjustments) and resilient members 70 that provide some amount of tension, holding the cannula 40 in place, and therefore, retaining the interface pillows 10 within the wearer's nostrils. For example, in some embodiments the resilient members 70 are made from medical grade silicone. The interface pillows 10 are describe in detail along with FIGS. 2 and 3.

Note that interface pillows of the prior art are typically made of a very soft and pliable material and have an overall round cross-sectional shape. When such is inserted into the nostril of a wearer, the round shape must conform to an internal shape of the user's nostrils, leading to both discomfort and impacted air passages that result in higher velocity of air flow and noise.

Figure 2:
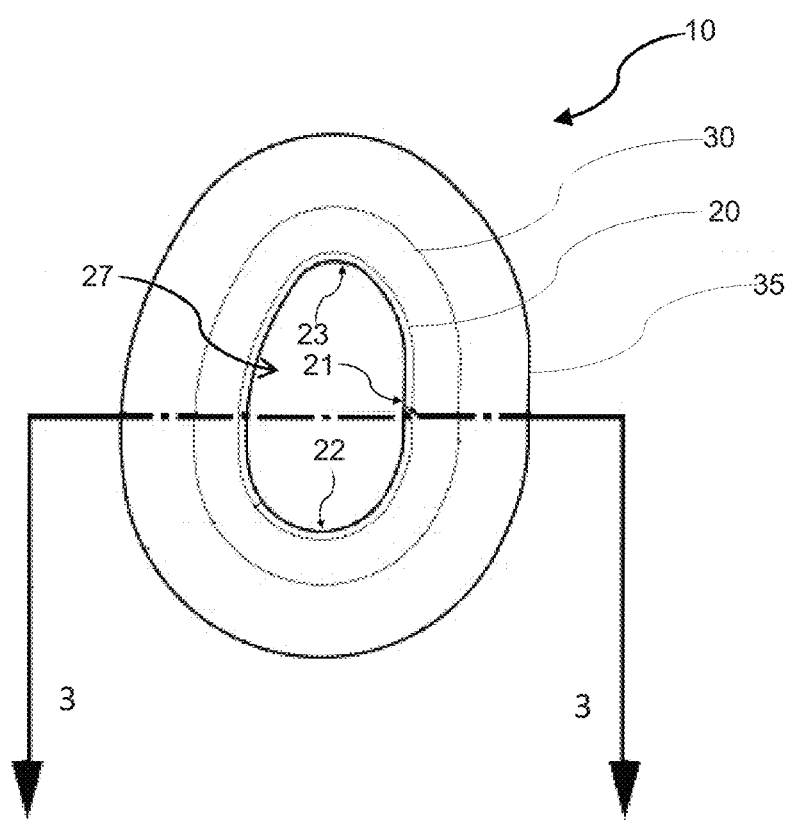
FIG. 2 illustrates a bottom plan view of a pillow interface of the present invention.
Figure 3:
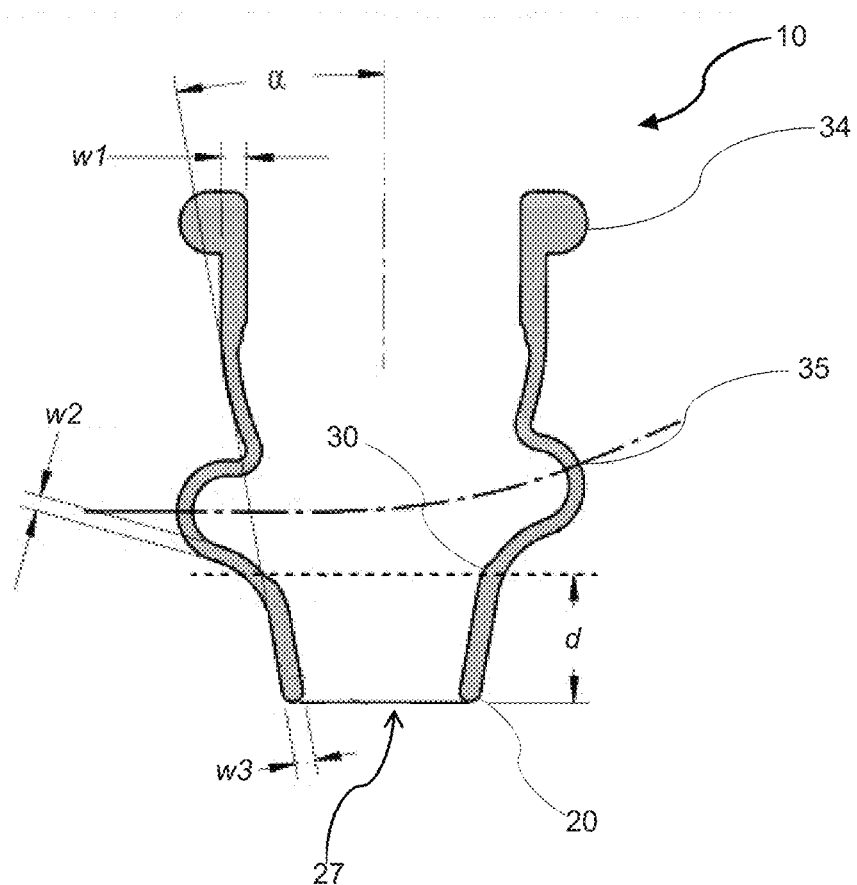
FIG. 3 illustrates a cross-sectional view of the pillow interface of FIG. 2 along lines 3-3.

Referring to FIGS. 2 and 3 a bottom plan view and a cross-sectional view of the interface pillows 10 is shown. The interface pillows 10 fit into and against the outer portion (entry area) of the wearer's nostrils. In general, the interface pillows 10 are made as pliable members (e.g. deform slightly under pressure) having a body that is elongated with one end for interfacing with a cannula 40 and a distal end for insertion partially into a wearer's nostril.

Viewing one interface pillow 10 from the bottom (FIG. 2), the insertion depth, d, is defined by a side that slopes outwardly from the insertion end 20 to a point of insertion 30. The insertion slope is an angle, α, that in some embodiments is 10 degrees from a center axis of the interface pillow 10. Proper insertion is limited by an insertion bulge 35 that prevents over-insertion of the interface pillows 10 into the nostrils of the wearer. Each interface pillow 10 has a seal 34 (sealing end) for sealing to the cannula 40 (see FIGS. 4-6). In some embodiments, the insertion depth, d, is set at approximately 0.25" for maximum comfort and sealing against within the patient's nostril.

The cross-sectional shape of the interface pillow 10 is formed to provide an enhanced seal within the wearer's nostril while providing maximum comfort. Note that the view from the bottom shown in FIG. 2 is that of an interface pillow 10 that is to be worn in the left nostril, as the interface pillow 10 that is to be worn in the right nostril is flipped to match the symmetry of the wearer's nose.

The cross-sectional shape of the interface pillow 10 is shown having three specific areas 21/22/23. The septum interface area 21 is flattened to rest comfortably against the wearer's septum when inserted into the left nostril. The upper interface area 23 is rounded and narrow with respect to the lower interface area 22, as the geometry/shape of most nostrils are wider towards the mouth of the wearer than they are towards the brow of the wearer. In this, the lower interface area 22 is the widest, dilating the lower region of the wearer's nostril the most, as the lower region of the wearer's nostril is the least sensitive.

This shape of the insertion area provides both a good seal and improved comfort. This shape of the insertion area enable the interface pillows 10 to be made of a stiffer or thicker material than those of the prior art. In such, upon insertion into the nostrils, the interface pillows 10 retain their shape and, therefore, do not restrict air flow through the air channel 27. Further, testing has shown that the shape of the insertion area of the interface pillows 10 maintains a seal even at the highest pressures possible with existing air pressure sources, typically around 20 centimeters of water pressure.

The insertion area of the cushion which fits against the inside of the nostrils is at an angle, α, that in some embodiments is 10 degrees from a center axis of the interface pillow 10. When the interface pillow 10 is pressed against the nostrils, the inside of the nostril remains steadfast while the outside of the nostril (nose) gives way slightly, approximately 0.10 inch.

In FIG. 3, a cross section of one interface pillow 10 is shown. This illustrates shows that the insertion end 20 of the interface pillow 10 is angled at an angle of α to relieve an amount of pressure from being exerted against the septum. This excess pressure is experienced because the outside of the nose will give way approximately 0.10" while the septum remains stationery. This feature compensates for the uneven distribution of pressure against the bottom of the nostrils while in use. The result is significantly greater comfort, and much greater seal capacity with much less chance of an air leak.

In some embodiments, the wall thicknesses vary. In such, at the insertion end 20, the insertion wall thickness w3 is 0.04" and narrows to 0.04" at the insertion bulge 35. These dimensions promote a forgiving feel of the pillows cushion against the bottom of the nose, while maintaining an open air way of the insertion end 20 when inserted into the nostrils. At the seal 34, the thickness is, for example, 0.05"

Figure 4:
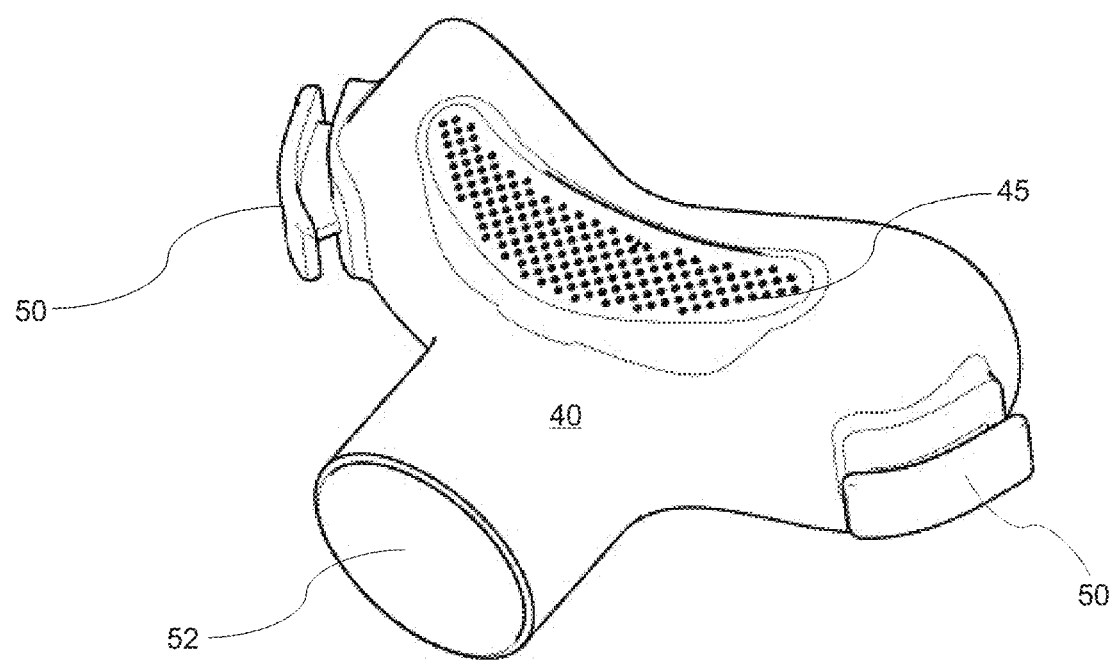
FIG. 4 illustrates a perspective view of the cannula of the present invention.
Figure 5:
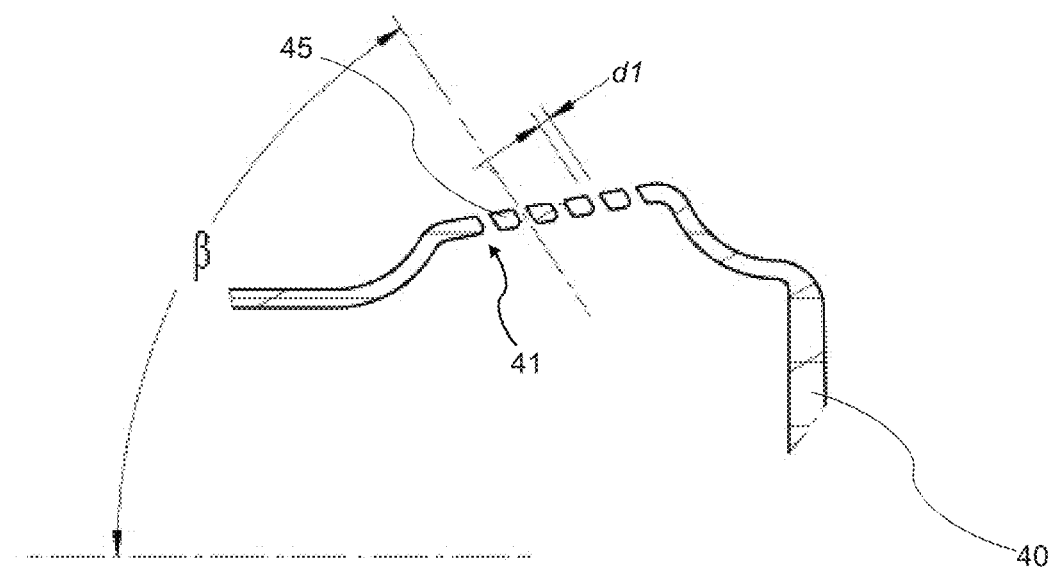
FIG. 5 illustrates a cut-away partial view of the cannula of the present invention.
Figure 6:
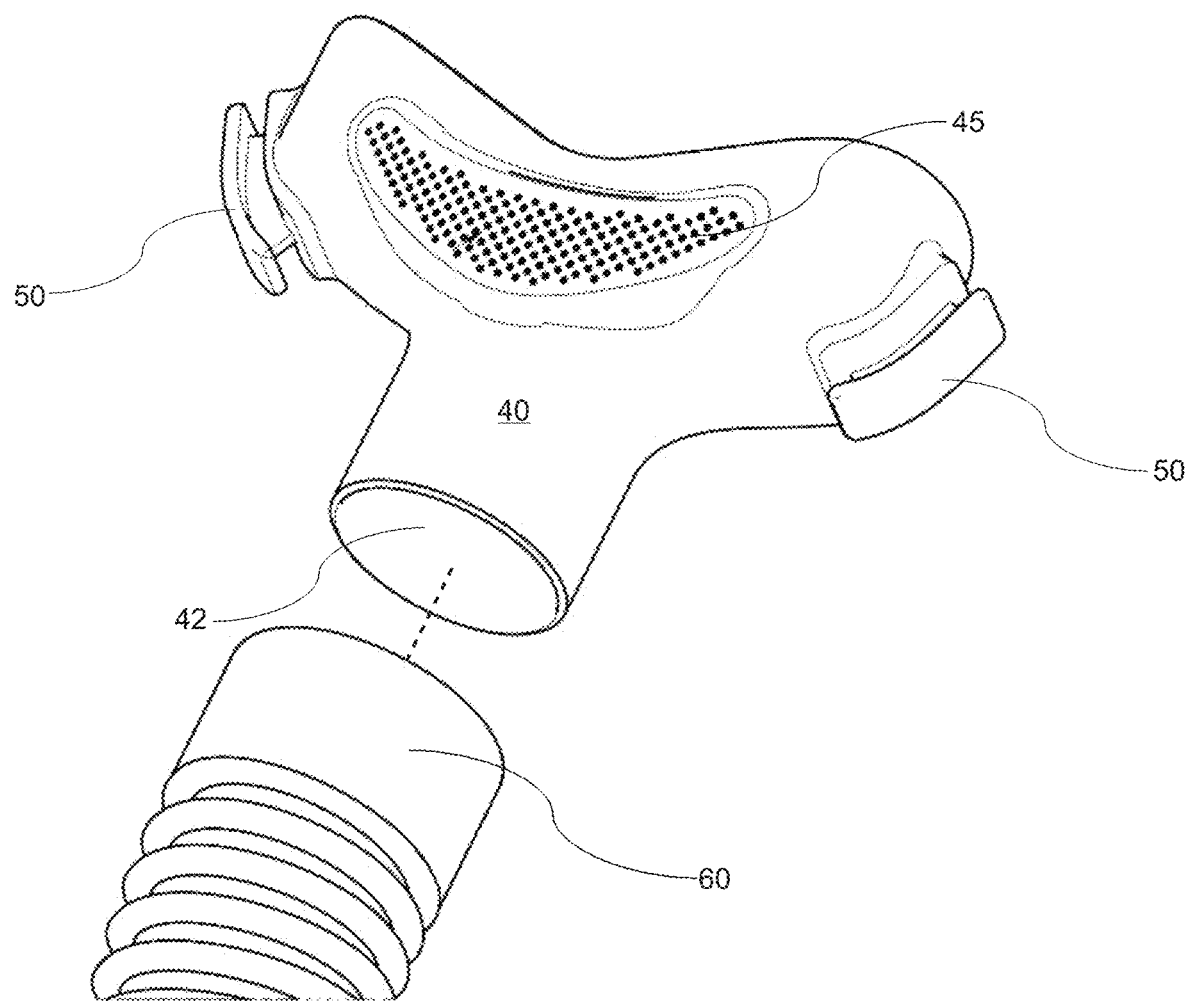
FIG. 6 illustrates a perspective view of the cannula of the present invention being connected to a source of air flow.

Referring to FIGS. 4 through 6, perspective views of the cannula 40 of the present invention are shown. The cannula 40 is preferably hollow. The bleed port section 45 of the cannula 40 allows the user to exhale. The bleed port section 45 is placed in the front of the cannula body and directs exhalation air flow in a direction away from the arms/hands of a wearer, especially when the wearer is sleeping on their side. The exhaled air flow is directed at an angle, β, which is, for example, 57 degrees with respect to a lengthwise axis of the cannula 40. The bleed port section 45 is composed of bleed holes 41, each having an internal diameter, for example an internal diameter of 0.02". In some embodiments, there are approximately 160 bleed holes 41. This provides a 0.05" square inch cross-sectional flow space per bleed hole 41 which is equivalent to a 0.25" diameter bleed hole. This flow space for exhaled air is much greater than that of the prior art. This flow space eliminates, or greatly reduces, work of breathing. This volume of flow space for exhaled air is possible because of the high volume of incoming air made available through the open flow space within the interface pillows 10.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An interface pillow for insertion into a nostril of a user, the interface pillow comprising:
   a pliable member having a body, the body having an insertion end and a distal sealing end, the distal sealing end having a seal for interfacing with a cannula whereas the body has a decreasing cross-sectional area from the sealing end to the insertion end;
   an insertion bulge extending from the body limiting an insertion distance;
   an insertion area of the body extending between the insertion end and the insertion bulge, the insertion area having sides that angle inwardly towards the insertion end at an angle, thereby a cross-sectional area of the insertion end being smaller than a second cross-sectional area at a point where the insertion area interfaces to the insertion bulge;
   whereas the outer shape of the insertion area is planar on one side for interfacing with a septum of a nose, and an upper interface area of the outer shape of the insertion area is narrower than a lower interface area of the outer shape of the insertion area to conform to a shape of a nostril of the nose; and
   whereas the insertion bulge is configured to seal against an outer edge of the nostril of the nose.

2. The interface pillow of claim 1, wherein the angle is 10 degrees.

3. The interface pillow of claim 1, wherein a first thickness of the body at the distal sealing end is greater than a second thickness of the body at the insertion area.

4. The interface pillow of claim 3, wherein the second thickness of the body at the insertion area is greater than a third thickness of the body at the insertion bulge.

5. The interface pillow of claim 4, wherein the first thickness of the body at the distal sealing end is 0.05 inches, the second thickness of the body at the insertion area is 0.04 inches and the third thickness of the body at the insertion bulge is 0.03 inches.

6. The interface pillow of claim 1, wherein a length of the insertion area is 0.25 inches.

7. An interface pillow for insertion into a nostril of a user, the interface pillow comprising:
   a pliable member having a body, the body having an insertion end and a distal sealing end, the distal sealing end having a seal for interfacing with a cannula whereas the body has a decreasing cross-sectional area from the sealing end to the insertion end;
   an insertion bulge extending from the body limiting an insertion distance to approximately 0.25 inches;
   an insertion area of the body extending between the insertion end and the insertion bulge, the insertion area having sides of approximately 0.25 inches in length, the sides taper inwardly towards the insertion end at an angle, thereby a cross-sectional area of the insertion end being smaller than a second cross-sectional area at a point where the insertion area interfaces to the insertion bulge;

whereas the outer shape of the insertion area is flatter on one side than an opposing side for interfacing with a septum of a nose, and an upper area of the outer shape of the insertion area is narrower than a lower area of the outer shape of the insertion area to conform to a shape of a nostril of the nose; and whereas the insertion bulge is configured to seal against an outer edge of the nostril of the nose.

8. The interface pillow of claim 7, wherein the angle is 10 degrees.

9. The interface pillow of claim 7, wherein a first thickness of the body at the distal sealing end is greater than a second thickness of the body at the insertion area.

10. The interface pillow of claim 9, wherein the second thickness of the body at the insertion area is greater than a third thickness of the body at the insertion bulge.

11. The interface pillow of claim 10, wherein the first thickness of the body at the distal sealing end is 0.05 inches, the second thickness of the body at the insertion area is 0.04 inches and the third thickness of the body at the insertion bulge is 0.03 inches.

* * * * *